United States Patent [19]
Nitzan et al.

[11] Patent Number: 6,120,459
[45] Date of Patent: Sep. 19, 2000

[54] METHOD AND DEVICE FOR ARTERIAL BLOOD PRESSURE MEASUREMENT

[76] Inventors: Meir Nitzan, Beit El DN Mizrach, Binyamin 90631; Louis Bloch, 9 Briel Beltra, Jerusalem 93695, both of Israel

[21] Appl. No.: 09/328,406

[22] Filed: Jun. 9, 1999

[51] Int. Cl.$^7$ ...................................................... A61B 5/02
[52] U.S. Cl. ......................... 600/493; 600/490; 600/485
[58] Field of Search ...................................... 600/481, 485, 600/486, 490, 493, 494, 495, 500, 504

[56] References Cited

U.S. PATENT DOCUMENTS

| | | |
|---|---|---|
| 4,331,155 | 5/1982 | Sacks . |
| 4,425,920 | 1/1984 | Bourland et al. . |
| 4,437,470 | 3/1984 | Prost . |
| 4,807,638 | 2/1989 | Sramek .................................. 600/485 |
| 4,821,734 | 4/1989 | Koshino . |
| 4,860,759 | 8/1989 | Kahn et al. . |
| 5,152,296 | 10/1992 | Simons . |
| 5,253,645 | 10/1993 | Friedman et al. ...................... 600/309 |
| 5,269,310 | 12/1993 | Jones et al. . |
| 5,309,908 | 5/1994 | Friedman et al. ...................... 600/694 |
| 5,423,322 | 6/1995 | Clark et al. . |
| 5,564,427 | 10/1996 | Aso et al. ............................... 600/309 |
| 5,755,669 | 5/1998 | Oho et al. .............................. 600/494 |
| 5,776,071 | 7/1998 | Inukai et al. ........................... 600/493 |
| 5,862,805 | 6/1999 | Nitzan .................................... 600/479 |
| 5,865,756 | 2/1999 | Peel, III ................................. 600/490 |

OTHER PUBLICATIONS

Marmor et al, "Method for Noninvasive Measurement of Central Aortic Systolic Pressure", *Clin. Cardiol.*, 10: 215–221, 1987.

Geddes et al, "Pulse Arrival Time as a Method of Obtaining Systolic and Diastolic Blood Pressure Indirectly", *Medical & Biological Engineering & Computing*, pp. 671–672, Sep., 1981.

Sharir et al, "Validation of a Method for Noninvasive Measurement Central Arterial Pressure", *Hypertension*, 21(1): 74–82, 1993.

*Primary Examiner*—Cary O'Connor
*Assistant Examiner*—Navin Natnithithadha
*Attorney, Agent, or Firm*—Mark M. Friedman

[57] ABSTRACT

A method of measurement of arterial diastolic blood pressure includes generating first and second signals indicative, respectively, of cardiac induced pulsatile variations in tissue blood volume in a first region and a second region of the subject's body. These signals are then processed to derive values of a delay between pulses in the first signal and corresponding pulses in second signal. A baseline value of the delay is evaluated, preferably in the absence of externally applied pressure. A variable pressure is applied to a third region of the subject's body so as to affect blood flow through at least one artery in the third region, the variable pressure being varied as a function of time. The first, second and third regions of the subject's body are chosen such that the delay varies as a function of the variable pressure. The diastolic pressure is then identified as a value of the variable pressure corresponding to a predefined non-zero value of the delay measured relative to the baseline value.

17 Claims, 17 Drawing Sheets

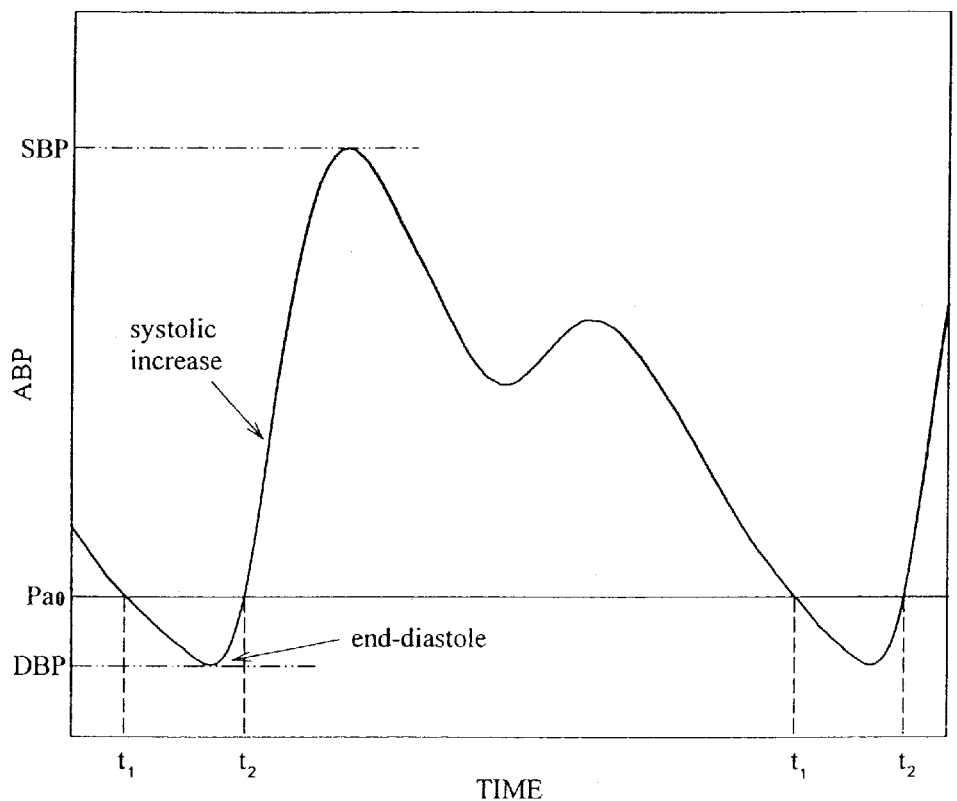
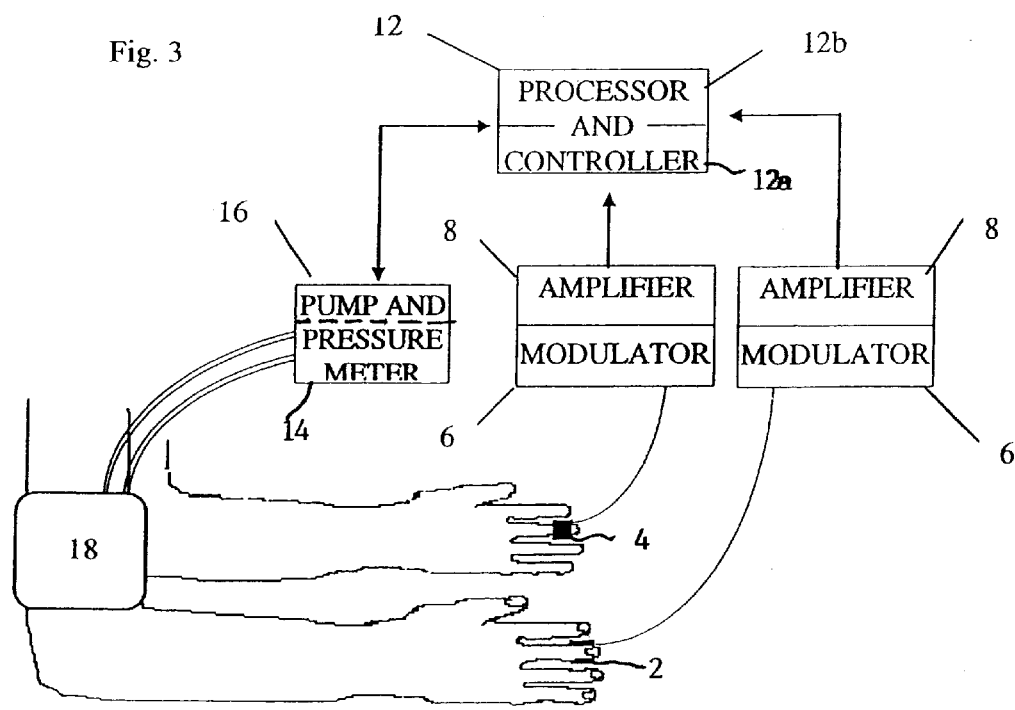
Fig. 3
Fig. 4

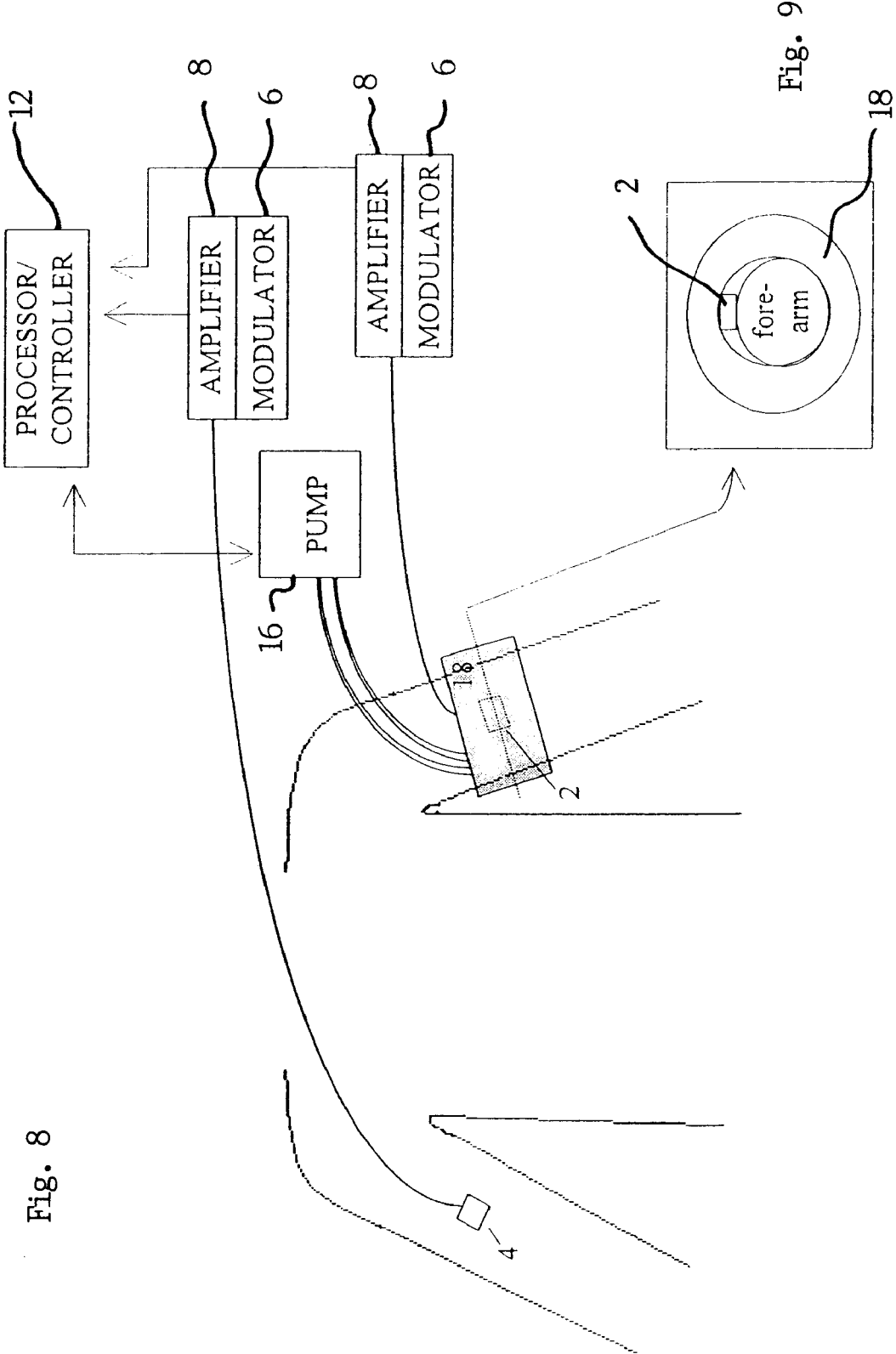

METHOD AND DEVICE FOR ARTERIAL BLOOD PRESSURE MEASUREMENT

FIELD AND BACKGROUND OF THE INVENTION

The present invention relates to a method and device for the measurement of arterial blood pressure (ABP). More particularly, the present invention relates to a method and a device for measuring systolic and diastolic blood pressure.

Blood supply to the tissues of a living body is essential for maintaining their metabolism and proper function. During systole (heart contraction), blood is ejected from the heart into the arterial system, thereby increasing the arterial blood pressure. The maximal arterial blood pressure (ABP) is the systolic blood pressure (SBP). During and after systole, blood flows from the arteries, through the capillaries, into the veins, and from them back into the heart. The period between two systoles is called diastole. During diastole, the arterial blood pressure decreases; the minimal arterial blood pressure (at the end of diastole) is called diastolic blood pressure (DBP).

Similar to blood pressure, blood volume in the tissue also shows oscillations at the heart rate. During systole, blood is ejected from the left ventricle into the peripheral tissues, thereby increasing their blood content. The measurement of the cardiac induced changes of tissue blood volume is called plethysmography, which can be performed by means of several methods, including photoplethysmography (PPG), which is the measurement of light absorption in tissue. The PPG signal originates from the increase of tissue blood volume during systole, and the consequent higher light absorption. FIG. 1 shows a known PPG probe attached to a finger. The light source L emits light into the tissue and the photodetector D measures the light scattered from the tissue under the skin. The output of the photodetector depends on the tissue blood volume, and oscillates with the oscillations of the latter.

FIG. 2 shows the blood pressure and the PPG signal measured simultaneously in the finger arteries as a function of time. The blood pressure measurement was performed on a fingertip by means of a continuous, non-invasive blood pressure meter (Finapres, Ohmeda, U.S.A.). As can be seen in FIG. 2, the curve of oscillations (at the heart rate) of the tissue blood volume as measured by the PPG signal, is similar, but not identical, to the ABP curve.

Blood pressure can change because of exercise, mental stress, or excitement. It also changes spontaneously due to activity of the autonomic nervous system. For adults aged below 40 years, the values of normal blood pressure (at rest) are 120 mmHg and 80 mmHg for systolic and diastolic blood pressures, respectively; If the ABP is too high (hypertension), the subject is at higher risk of cerebral stroke and heart attack. Lower than normal blood pressure (hypotension) is acutely hazardous, since it may cause low blood supply to the brain, resulting in fainting or even in brain damage. Decreasing blood pressure for patients after trauma, surgery or heart attack is an indication of cardiovascular deterioration.

Blood pressure can be measured invasively by inserting a catheter into an artery and measuring the pressure by means of a piezoelectric device. This measurement is the most reliable one, and it is done in intensive care units where an arterial line is inserted for additional purposes. Due to its invasiveness, this method is not used for routine applications.

The auscultatory method is the most common method for non-invasive measurement of blood pressure, and is based on hearing (via stethoscope or microphone) the turbulence sounds which appear in a compressed artery when it is intermittently closed and opened by means of an inflatable cuff having air pressure of a value between that of diastolic and systolic blood pressure. Usually, the cuff air pressure is increased above the SBP, then decreased. The cuff air pressure at which the turbulence sounds appear is the SBP; the pressure at which the quality of the sounds changes, becoming muffled, is defined as the higher DBP (IV Korotkoff or phase IV DBP); the pressure at which they totally disappear is defined as the lower DBP (V Korotkoff or phase V DBP). In general the lower DBP has to be taken as the DBP, but for some groups of patients for whom the Korotkoff sounds are heard even for extremely low cuff pressure, such as in pregnant women, the higher DBP is taken. The manual auscultatory method (using a stethoscope) has been accepted as the gold standard for non-invasive ABP measurement, and is routinely used in clinics and hospitals. The automatic auscultatory method (using a microphone), is also used for monitoring ABP in hospital wards. Despite its extensive use, the auscultatory method is not accurate, both because of the difficulty in detecting the correct sounds and because of the unclear relationship between the disappearance of the turbulence sounds and DBP.

Automatic blood pressure measurement can also be done by means of the oscillometric method. A cuff is applied to the arm or finger and, besides the measurement of the average air pressure, the oscillatory variations of air pressure in the cuff are measured by means of a piezoelectric pressure transducer. Oscillations at the rate of the heart can then be seen in the cuff pressure (oscillometry) due to the cardiac induced changes in the arterial blood volume. In an alternative method, a sensor for detecting blood volume changes in the arteries, such as a PPG device, is attached to the skin under the cuff. Here too, oscillations at the rate of the heart appear in the volume sensor output (volume oscillometry). When the air pressure is continuously increased above diastolic blood pressure, these oscillations also increase until the air pressure is equal to the mean blood pressure, and then they decrease. The systolic and diastolic blood pressure can be derived from the curve of the amplitude of oscillation as a function of the air pressure, using empirical formulae. This method, which is called "oscillometry", can be used for monitoring blood pressure, but the measurement time is long: more than 20 heart beats, depending on the patient and on the required accuracy. In any case, the method and the commercial devices which are based thereon are not considered to be accurate.

The low accuracy of the automatic auscultatory and oscillometry methods for the measurement of diastolic and systolic blood pressure, and the need for a reliable automatic method, have resulted in several attempts to develop other methods for blood pressure measurements. Some of these methods are based on PPG measurement. The systolic blood pressure can be non-invasively measured by means of PPG, by using a PPG device and a cuff around the arm or finger, increasing the air pressure in the cuff, and determining the air pressure at which the PPG signal disappears. This air pressure is equal to the systolic blood pressure in the artery under the cuff. In principle, measurement of systolic blood pressure by PPG and a pressure cuff may be performed in a straightforward manner by identifying the onset of PPG pulses. Determination of the diastolic blood pressure from the PPG signal, on the other hand, is more difficult.

In U.S. Pat. No. 5,269,310, there is disclosed a method for measuring, by means of PPG, changes of blood volume in the arteries during systole together with the patient's blood pressure, and for determining what is assumed to be a constant k particular to the patient's arterial blood pressure-volume relationship. By means of this calibration, the DBP and SBP for each heartbeat is determined from the minimum and maximum points of the PPG signal. The method is not accurate, since DBP and SBP are not actually related to the maximum and minimum of the PPG signal by a constant k.

In U.S. Pat. No. 5,423,322, an exponential relationship is assumed between the ABP and the blood volume changes measured by PPG, for the assessment of the cardiac-induced blood pressure oscillations from the simultaneous blood volume oscillations in the heart rate. There are several drawbacks to this method, as will now be detailed.

Firstly, the relationship between the arterial blood pressure and the blood volume is not strictly exponential. In fact, the volume vs. pressure curve changes as a function of time, and even changes between the period of increasing pressure (systole) to the period of decreasing pressure (diastole) within the same cardiac cycle, as can be seen in FIG. 2 of the present application.

Secondly, the blood volume changes not only in a single artery, but also in the small arteries and in the arterioles (resistance vessels). It is not possible to simulate the entire group of arteries and arterioles as a single artery, since the pressure therein is not constant due to the reduction of the blood pressure from the arteries to the arterioles.

Another known method for continuous measurement of finger ABP is the arterial volume clamp method, which is based on PPG. The device utilized for this method is composed of a finger cuff with a PPG probe, and the method is based on the determination of the cuff air pressure which is required to keep the arterial blood volume constant. The device enables the measurement of ABP changes during the cardiac cycle via very rapid changes of the cuff air pressure. The method is very sophisticated, but it was not found to reliably record ABP. The device is expensive, due to the need to swiftly change the cuff air pressure in accordance with the blood pressure changes during the cardiac cycle.

Other methods for the measurement of ABP have been suggested, but the only methods which have been accepted for routine and comprehensive clinical use are the oscillometric and auscultatory methods, indicating that the other suggested methods are either not reliable enough, or are too complicated, for clinical use.

Another approach, suggested by a number of academic papers but not implemented in practice, proposes to measure diastolic blood pressure on the basis of a delay in the pulse caused by pressure from a cuff. Applying a pressure between diastolic and systolic blood pressure on an artery results in compression of the artery for part of the cardiac cycle time as can be seen in FIG. 3. As a result, the pressure pulse in the artery distal to the pressure application location will start later than in contralateral arteries not affected by the pressure. This approach was presented by L. A. Geddes et al. in a paper entitled "Pulse Arrival Time as a Method of Obtaining Systolic and Diastolic Blood Pressure Indirectly", (Medical & Biological Engineering & Computing, September 1981, 19:pp. 671–672). Geddes et al., experimenting on dogs, compared the measurements of an invasive pressure sensor in the leg of a dog with either another similar sensor in the contralateral leg or an ECG reference to detect a delay in the pulse reaching a location beyond a pressure cuff. The use of ECG as a time reference is particularly problematic, giving broad scattering of results. The measurement of the pulse delay due to the cuff pressure using ECG as a reference was also suggested by A. Marmor et al. (Clin. Cardiol. 1987, 10:215–221) and T. Sharir et al. (Hypertension 1993, 21: 74–82) for the determination of the systolic increase curve of arterial pressure as a function of time.

Even with a second sensor in the contralateral leg as a reference, the point at which the diastolic pressure is supposedly indicated appears poorly defined. Furthermore, the measurement of the time delay between the pulses in the two sides is inaccurate, since the time delay was identified as the time difference between the minima of the corresponding pressure pulses in the two sides. The measurement of the time of the pulse minimum is subject to significant error, since the curve in the neighborhood of the minimum changes slowly and a small error in the pressure measurement may result in a large error in the determination of the minimum time. This problem would be accentuated if the noninvasive method were used for the determination of the start of the pulse, in a peripheral region, since noninvasive measurement of any parameter which is related to the pulse pressure has a higher noise level than direct invasive measurement of arterial blood pressure. It should be noted that Geddes et al. claimed that it is possible to use a noninvasive technique to detect the start of the pressure pulse, and that they intend to do that, and to publish the results in a second paper. However, to the best of our knowledge, no such paper has ever been published. It seems that the analysis of the non-invasively achieved signal as suggested by Geddes did not permit accurate measurement of the diastolic blood pressure, possibly for the reasons discussed above.

There is therefore a need for a practical, non-invasive technique for measuring arterial diastolic blood pressure on the basis of a delay in pulses caused by a pressure cuff. It would also be highly advantageous to provide an automatic device for measuring arterial diastolic blood pressure according to such a technique.

SUMMARY OF THE INVENTION

The present invention is device and method for measurement of arterial blood pressure and, in particular, the diastolic blood pressure.

According to the teachings of the present invention there is provided, a method for measuring arterial diastolic blood pressure in a subject, the method comprising: (a) generating first and second signals indicative, respectively, of cardiac induced pulsatile variations in tissue blood volume in a first region and a second region of the subject's body; (b) processing the first and second signals to derive values of a delay between pulses in the first signal and corresponding pulses in second signal; (c) evaluating a baseline value of the delay; (d) applying a variable pressure to a third region of the subject's body so as to affect blood flow through at least one artery in the third region, the variable pressure being varied as a function of time, the first, the second and the third regions being chosen such that the delay varies as a function of the variable pressure; and (e) identifying a value of the variable pressure corresponding substantially to a predefined non-zero value of the delay measured relative to the baseline value.

In preferred cases, the phase IV DBP is identified directly by use of a value of the delay between about 30 and about 40 ms, and the phase V DBP is identified directly by use of a value of the delay between about 15 and about 25 ms.

According to a first preferred approach, the processing includes: (a) measuring a first amplitude of a first pulse of the first signal; (b) identifying a first point in the systolic increase portion of the first pulse at which the first signal reaches a predefined proportion of the first amplitude; (c)

measuring a second amplitude of a corresponding pulse of the second signal; (d) identifying a second point in the systolic increase portion of the corresponding pulse at which the second signal reaches the predefined proportion of the second amplitude; and (e) defining a value of the delay as the time between the first and the second points.

According to a second preferred approach, the processing includes: (a) calculating a time derivative of a first pulse of the first signal; (b) identifying a first maximum value of the time derivative in the systolic increase portion of the first pulse; (c) identifying a first point at which the time derivative reaches a predefined proportion of the first maximum value; (d) calculating a time derivative of a second pulse of the second signal; (e) identifying a second maximum value of the time derivative in the systolic increase portion of the second pulse; (f) identifying a second point at which the time derivative reaches a predefined proportion of the second maximum value; and (g) defining a value of the delay as the time between the first and the second points.

According to a third preferred approach, the processing includes: (a) for corresponding pulses of each of the first and second signals, (i) identifying a local minimum of the signal, (ii) fitting a negative gradient line to a predefined portion of the signal prior to the local minimum, (iii) fitting a positive gradient line to a predefined portion of the signal subsequent to the local minimum, and (iv) extrapolating the negative gradient line and the positive gradient line to determine an intersection, referred to as an adjusted minimum point of the signal; and (b) defining a value of the delay as the time between the adjusted minimum point of the first signal and the adjusted minimum point of the second signal.

According to a fourth preferred approach, the processing includes: (a) evaluating a measure of correlation between corresponding pulses of the first and second signals, the measure of correlation being evaluated as a function of a time shift of the second signal relative to the first signal; and (b) defining a value of the delay as the time shift which generates a maximum value of the measure of correlation.

According to a further feature of the present invention, the first and second signals are generated by use of non-invasive sensors, and preferably, photoplethysmography sensors.

There is also provided according to the teachings of the present invention, a device for measuring arterial diastolic blood pressure in a subject, the device comprising: (a) a pressure cuff applicable to a first region of the subject's body so as to affect blood flow through at least one artery in the first region; (b) a pressure controller operatively connected to the pressure cuff so as to vary a current pressure of the pressure cuff; (c) first and second plethysmography sensors for application to a second region and a third region of the subject's body, the first and second plethysmography sensors being configured to produce first and second signals, respectively, indicative of pulsatile variations in tissue blood volume in the second and third regions, respectively; and (d) a processor associated with the pressure controller and with the first and second plethysmography sensors, the processor being configured to: (i) process the first and second signals to derive values of a delay between pulses in the first signal and corresponding pulses in second signal, (ii) evaluate a baseline value of the delay corresponding to a current pressure substantially equal to ambient pressure, and (iii) identify as the diastolic pressure a value of the variable pressure corresponding substantially to a predefined non-zero value of the delay measured relative to the baseline value.

There is also provided according to the teachings of the present invention, a method for measuring arterial diastolic blood pressure in a subject, the method comprising: (a) generating first and second signals indicative, respectively, of cardiac induced pulsatile variations in tissue blood volume in a first region and a second region of the subject's body; (b) processing the first and second signals to derive values of a measure of correlation between pulses in the first signal and corresponding pulses in second signal; (c) applying a variable pressure to a third region of the subject's body so as to affect blood flow through at least one artery in the third region, the variable pressure being varied as a function of time, the first, the second and the third regions being chosen such that the measure of correlation varies as a function of the variable pressure; and (d) identifying a value of the variable pressure corresponding to a value of the measure of correlation substantially equal to a predefined value.

According to a further feature of the present invention, a baseline value of the measure of correlation is evaluated, the measure of correlation being adjusted on the basis of the baseline value such that the measure of correlation approaches 1 at low values of the variable pressure.

According to a further feature of the present invention, the predefined value is at least about 0.9.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 illustrates a prior art PPG probe attached to a finger of a subject;

FIG. 2 shows curves of the cardiac-induced oscillations of the blood pressure in a finger's arteries and the cardiac-induced oscillations of the tissue blood volume as a function of time;

FIG. 3 is a plot of arterial blood pressure as a function of time;

FIG. 4 is an illustration of an embodiment of the device for diastolic blood pressure measurement according to the present invention;

FIG. 5 is a block diagram of the device of FIG. 4;

FIG. 6 shows curves of PPG signals in the fingers of the right and left hands of a subject, for different air pressures applied to the subject's right arm;

FIG. 7 illustrates a further embodiment of the device for diastolic blood pressure measurement;

FIG. 8 illustrates a still further embodiment of the device for diastolic blood pressure measurements;

FIG. 9 is a cross-sectional view of the pressure application means and the PPG probe of FIG. 8;

FIG. 10 illustrates a first example of a technique for measuring time delay between corresponding pulses of two PPG signals according to the present invention;

FIG. 11 illustrates a second example of a technique for measuring time delay between corresponding pulses of two PPG signals according to the present invention;

Figure 10:
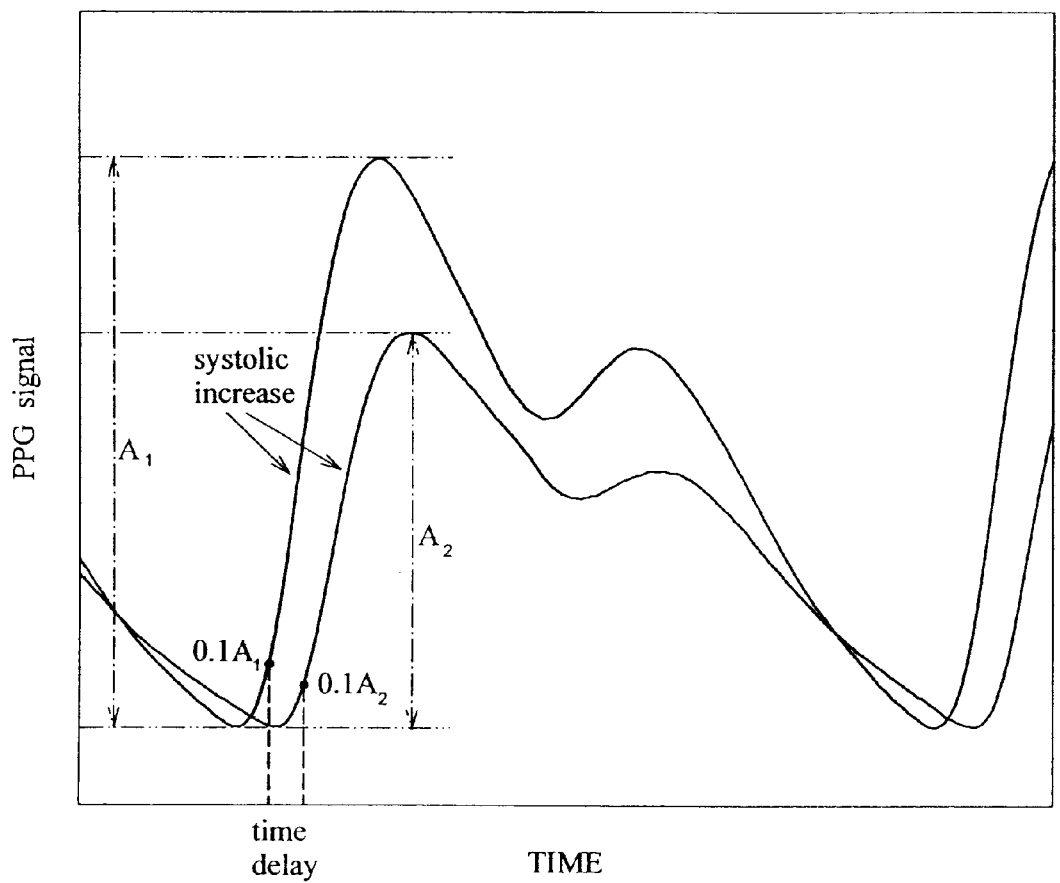
Figure 11:
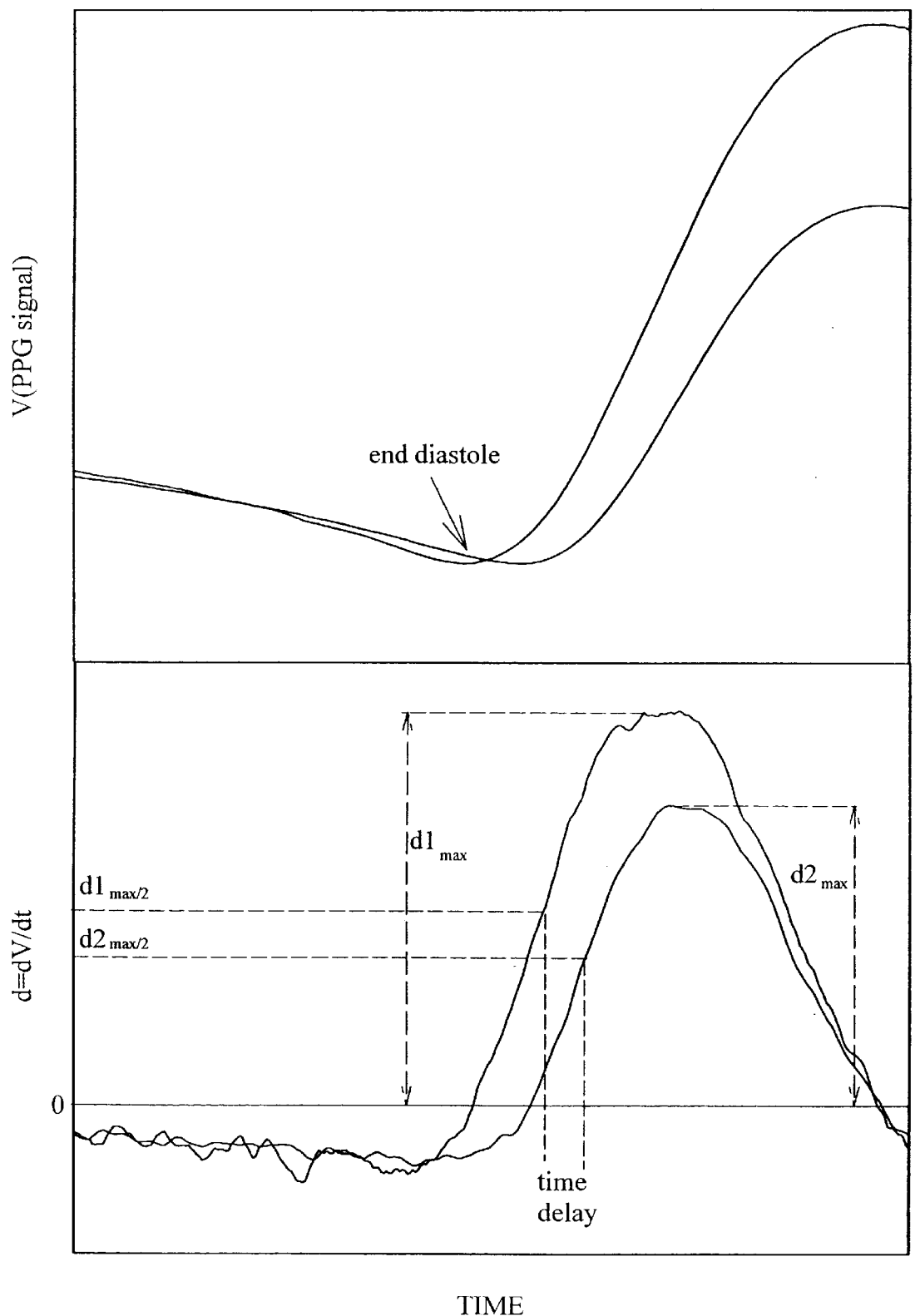
Figure 12:
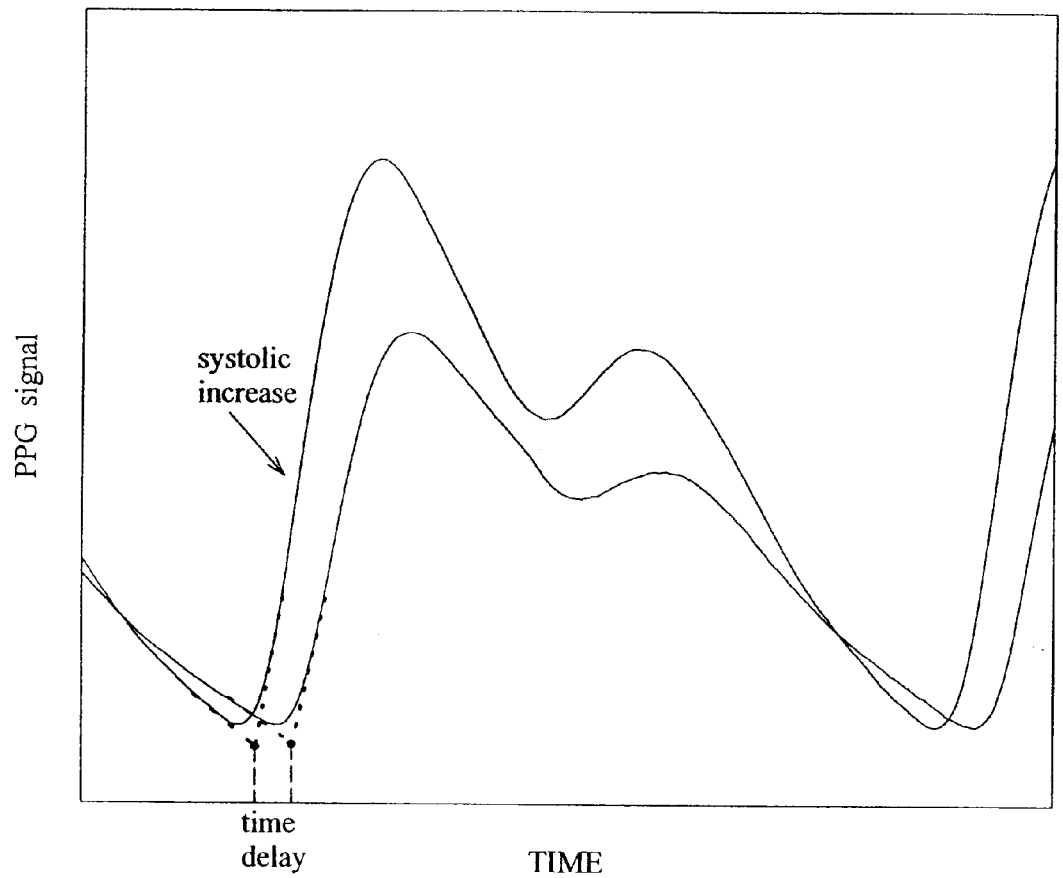
Figure 13:
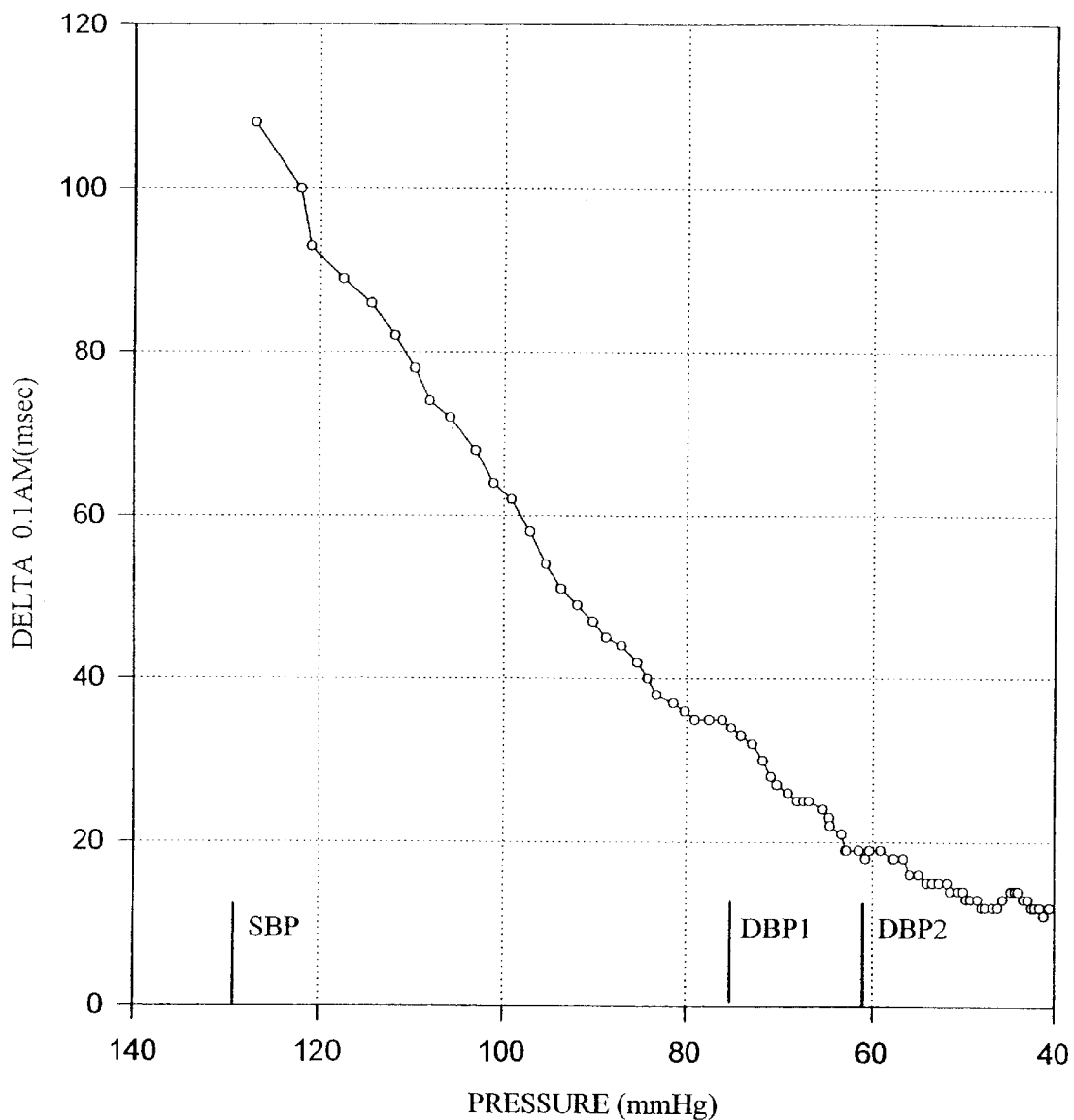
Figure 14:
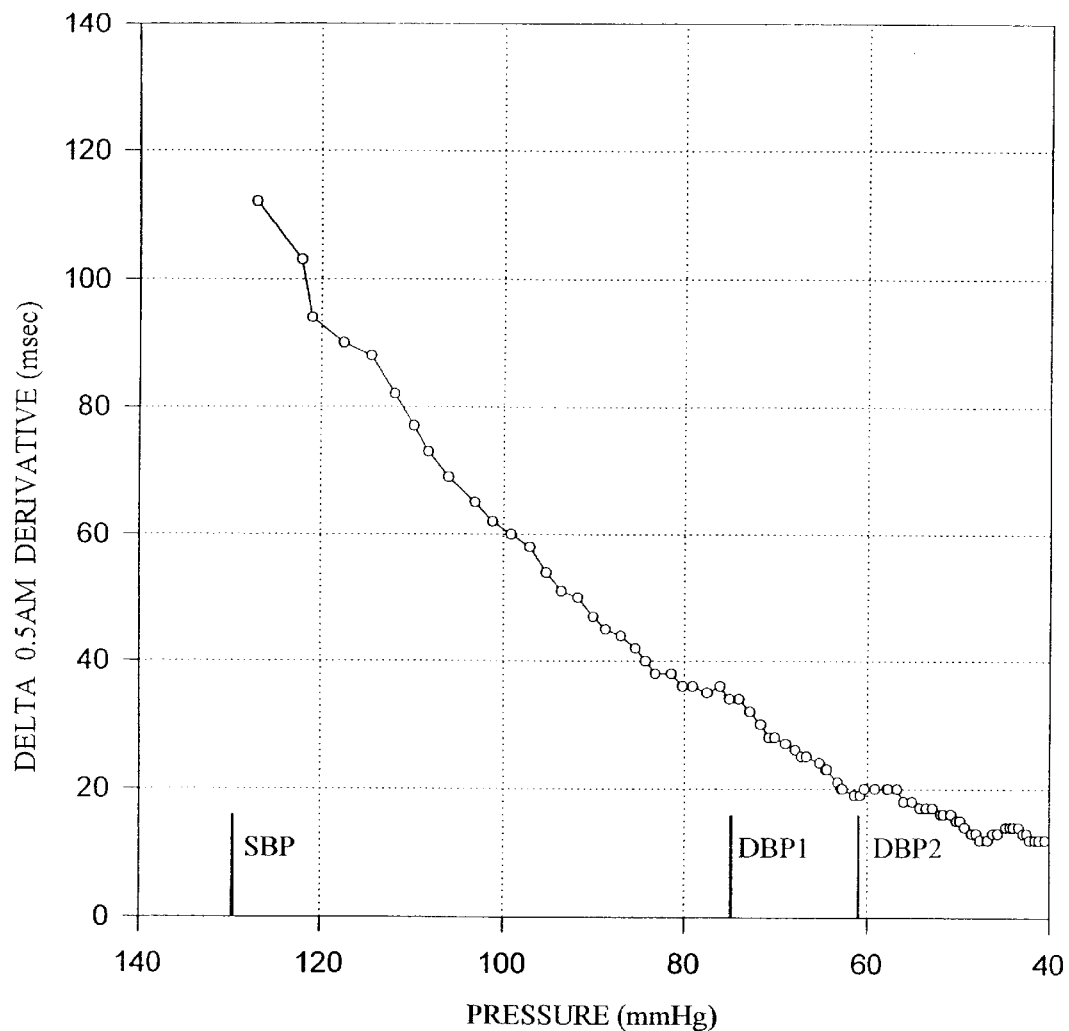
Figure 15:
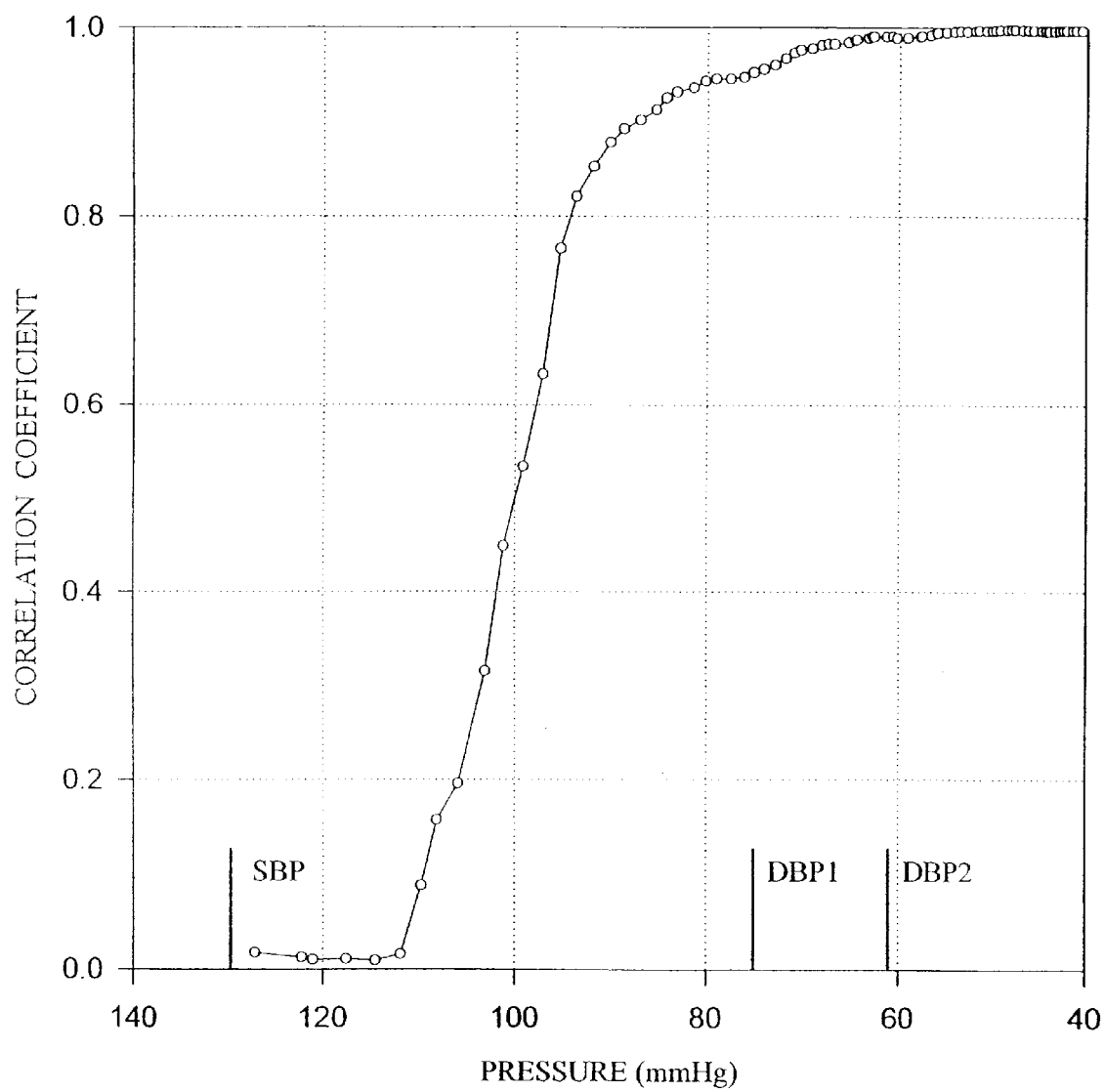
Figure 16:
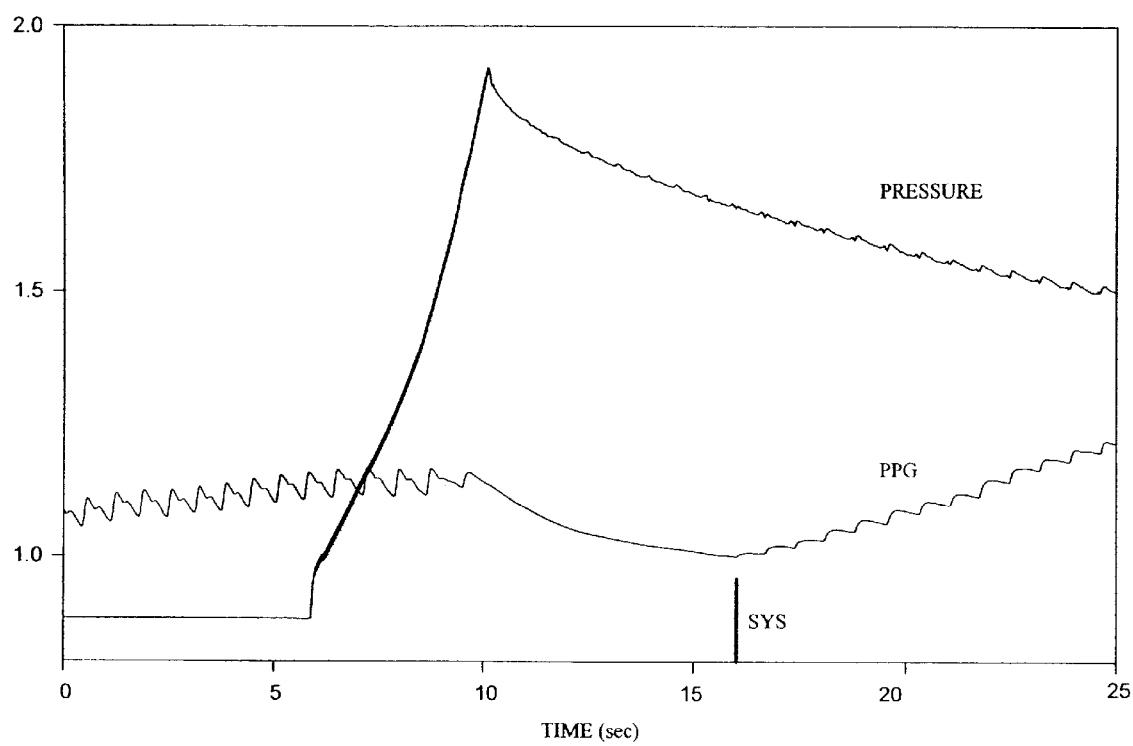
Figure 17A:
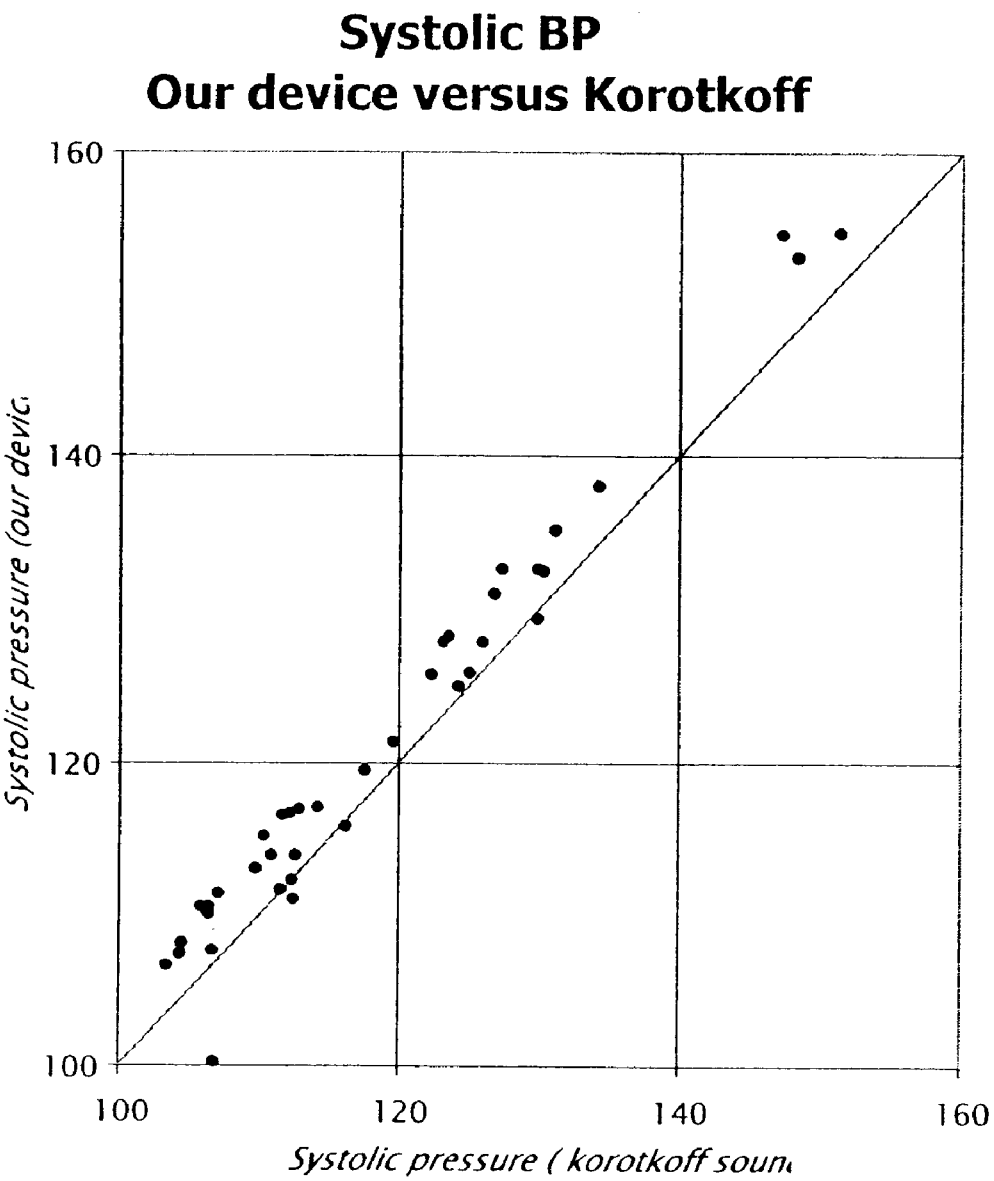
Figure 17B:
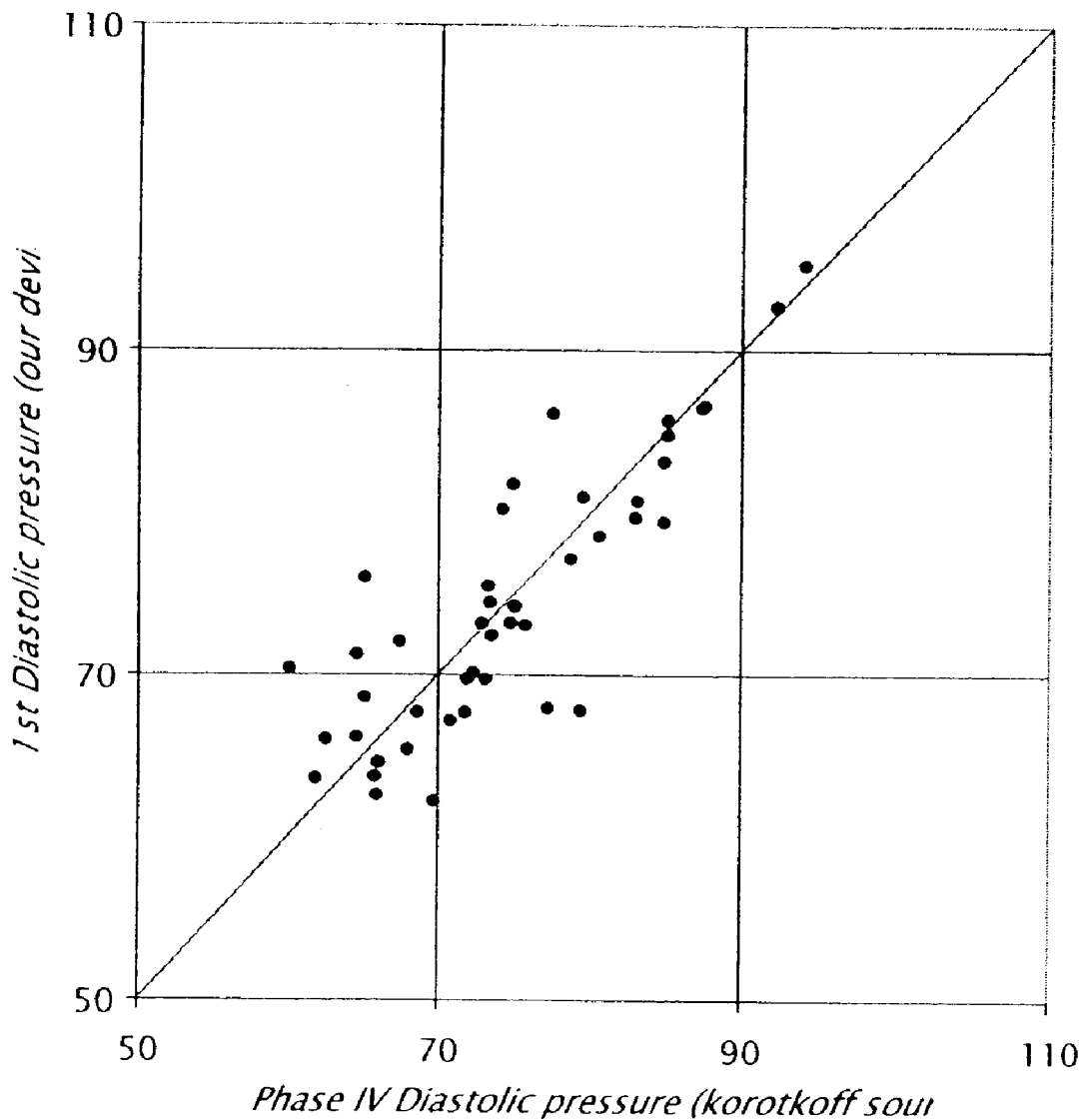
Figure 17C:
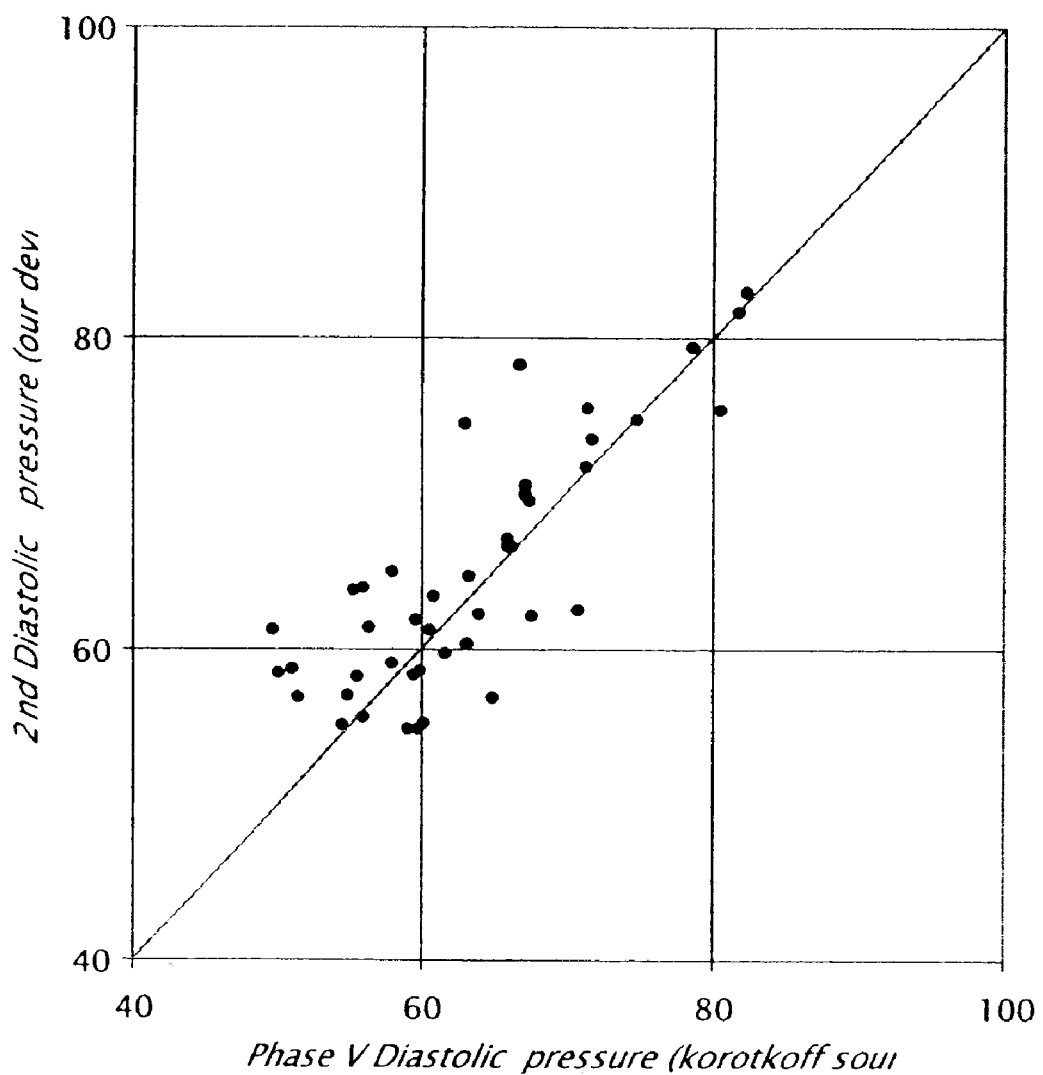
Figure 18:
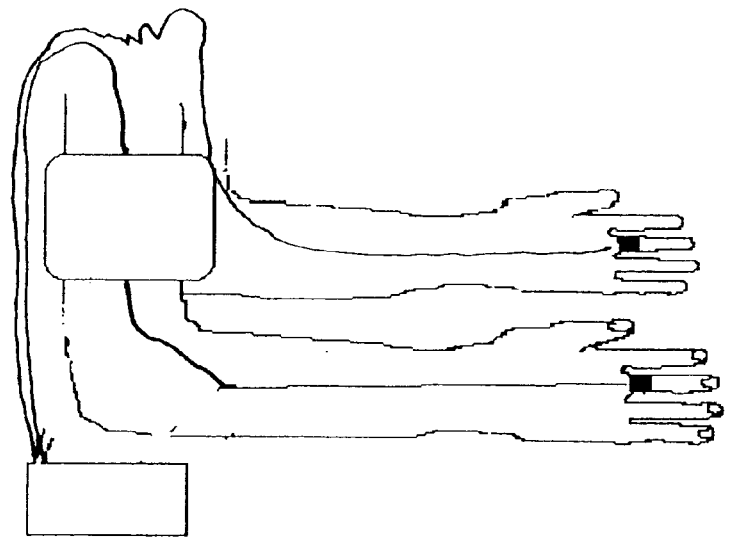
Figure 19:
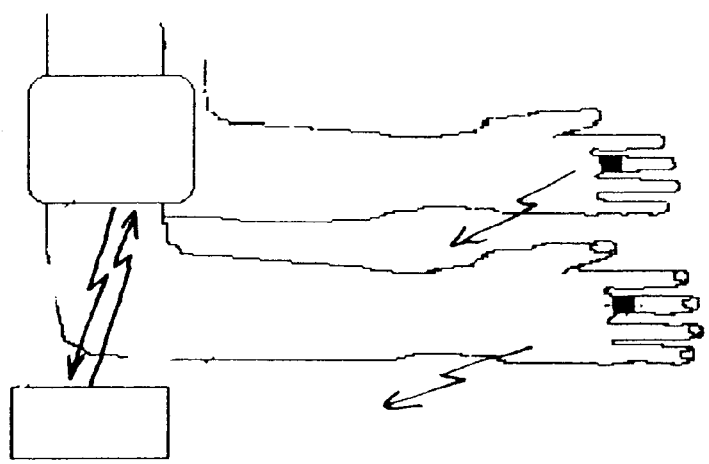

FIG. 12 illustrates a third example of a technique for measuring time delay between corresponding pulses of two PPG signals according to the present invention;

FIG. 13 illustrates results of time delay measurements as a function of applied cuff pressure obtained by the technique of FIG. 10;

FIG. 14 illustrates results of time delay measurements as a function of applied cuff pressure obtained by the technique of FIG. 11;

FIG. 15 illustrates a correlation function taken between two PPG signals as a function of applied cuff pressure;

FIG. 16 shows variations in both applied cuff pressure and an affected PPG signal over a given time period;

FIGS. 17A, 17B and 17C show comparisons of arterial blood pressure measurements obtained by the methods of the present invention and by conventional sphygmomanometry for systolic, first diastolic and second diastolic blood pressures, respectively;

FIG. 18 shows a first implementation of the device of FIG. 4 for use in blood pressure monitoring; and FIG. 19 shows a second implementation of the device of FIG. 4 for use in blood pressure monitoring.

DESCRIPTION OF THE PREFERRED EMBODIMENTS

The present invention is a device and method for measurement of arterial blood pressure and, in particular, the diastolic blood pressure.

The principles and operation of devices and methods according to the present invention may be better understood with reference to the drawings and the accompanying description.

Referring now to the drawings, FIGS. 4, 5 and 7–9 show various embodiments of a device, constructed and operative according to the teachings of the present invention, for measuring the arterial blood pressure of a subject.

Generally speaking, the invention is based on the application of a pressure cuff with air pressure Pa around the limb of a subject on a pressure application site, and a first PPG probe on a measurement site, distal to the pressure application site, said first PPG probe producing the first PPG signal. When the cuff is inflated to an air pressure above the SBP, the arteries under the cuff will be compressed and closed. Hence, the SBP can be measured by determining the air pressure at which the PPG signal disappears, as described above. When the cuff air pressure is held at a given value of $Pa_0$, which is below the SBP but above the DBP (see FIG. 3), the arteries under the cuff are compressed and closed for those short periods of time (between $t_1$ and $t_2$) in which the arterial blood pressure is below the cuff air pressure $Pa_0$. During the time at which the blood pressure decreases below the applied air pressure $Pa_0$, the blood stops flowing through the momentarily closed artery and no systolic increase in the tissue blood volume occurs, resulting in a reduction in said first PPG signal amplitude and a delay in the start of the systolic increase in said first PPG signal. Both the change in the PPG amplitude and the delay of the systolic increase are not easy to detect, since the PPG signal changes spontaneously. This small change in the first PPG signal can, however, be detected by measuring the first PPG signal simultaneously with a second (reference) PPG signal in a second PPG probe, which is not placed distal to the cuff so that it is not directly affected by the cuff, and comparing the two PPG signals. When the air pressure reaches a value between that of the diastolic and systolic blood pressure, the first PPG signal in the site distal to the cuff is delayed relative to the second (reference) signal of the second PPG probe, the length of the time delay increasing as the cuff pressure increases.

As mentioned above in the context of the work of Geddes et al., determination of the diastolic blood pressure from measurements of the delay between two such signals is non-trivial. By providing a combination of initial baseline time-delay determination, effective algorithms for evaluating the delay, and parameters determined by extensive experimentation, most preferred implementations of the present invention offer an accurate, repeatable and experimentally verified device and technique for measuring diastolic blood pressure, as will be described.

Thus, the method of the present invention includes generating first and second signals indicative, respectively, of cardiac induced pulsatile variations in tissue blood volume in a first region and a second region of the subject's body. These signals are then processed to derive values of a time-delay between pulses in the first signal and corresponding pulses in second signal. The delay may be calculated by application of one or more algorithm, selected examples of which will be described below. A baseline value of the delay is evaluated in the absence of externally applied pressure. A variable pressure is applied to a third region of the subject's body so as to affect blood flow through at least one artery in the third region, the variable pressure being varied as a function of time. The first, second and third regions of the subject's body are chosen such that the delay between the first and second signals varies as a function of the variable pressure applied to the third region. The diastolic pressure is then identified as a value of the variable pressure corresponding substantially to a predefined non-zero value of the delay measured relative to the baseline value.

In structural terms, with reference to FIG. 4, the invention provides a device for measuring arterial blood pressure in a subject, including a pressure cuff 18 applicable to a first region of the subject's body so as to affect blood flow through at least one artery in the first region, and a pressure controller 12a operatively connected to the pressure cuff so as to vary a current pressure of pressure cuff 18. First and second plethysmography sensors 2 and 4, applicable to two regions of the subject's body, are configured to produce first and second signals, respectively, indicative of systolic pulsatile variations in tissue blood volume in the corresponding regions. A processor 12b is associated with pressure controller 12a, optionally in a single unit 12, and with first and second plethysmography sensors 2 and 4. Processor 12b is configured to: (i) process the first and second signals to derive values of a delay between pulses in the first signal and corresponding pulses in second signal, (ii) evaluate a baseline value of the delay corresponding to a current pressure substantially equal to ambient pressure, (iii) identify a current value of the variable pressure corresponding to each value of the delay, and (iv) identify as the diastolic pressure a value of the variable pressure corresponding substantially to a predefined non-zero value of the delay measured relative to the baseline value.

It will be noted that sensors 2 and 4 may be applied to any two regions of the subject's body chosen such that the time delay obtained varies as a function of the pressure applied to cuff 18. In the case of FIG. 4, the reference signal from sensor 4 is substantially unaffected by variations in the applied pressure. In alternative implementations such as that of FIG. 7, the two regions in which measurements are taken may both be affected so long as they are affected to a different extent, thereby also allowing measurement of a time delay which varies as a function of the applied pressure.

Figure 1:
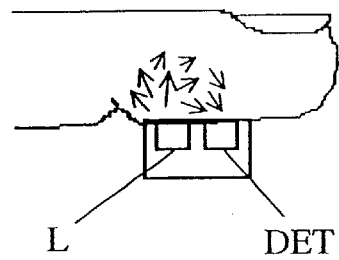
Figure 2:
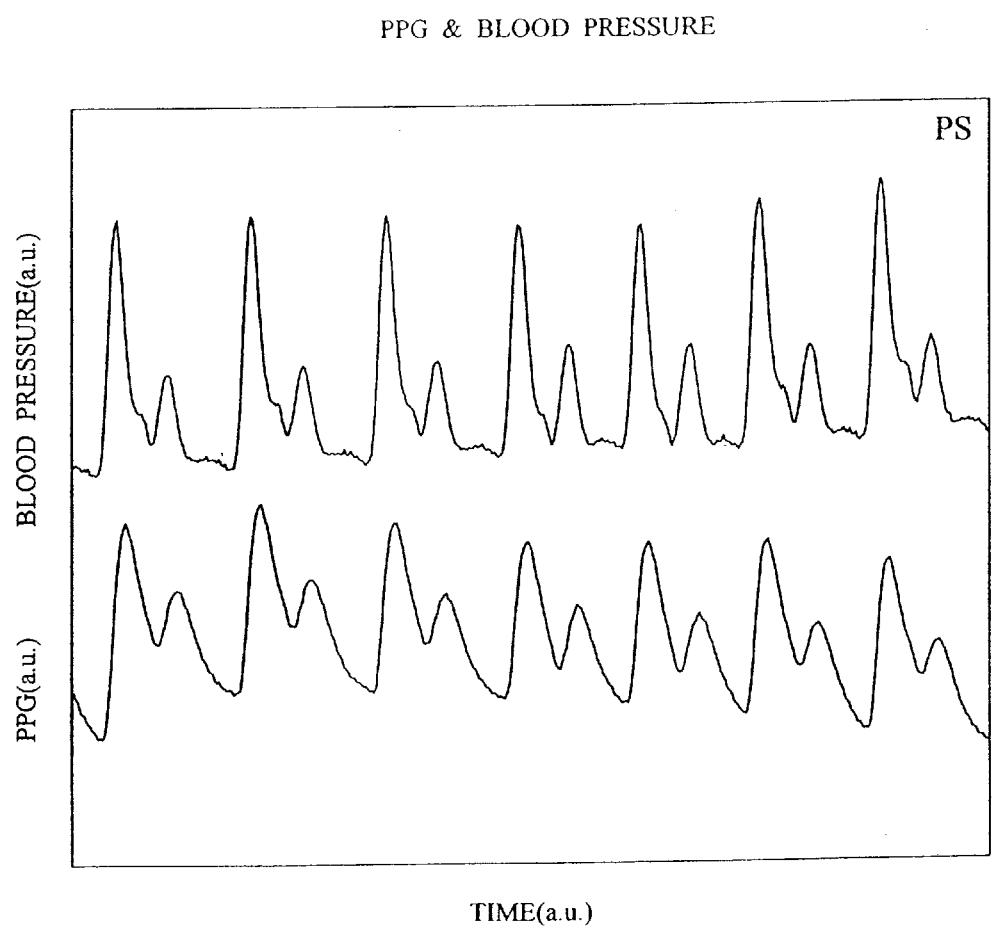
Figure 5:
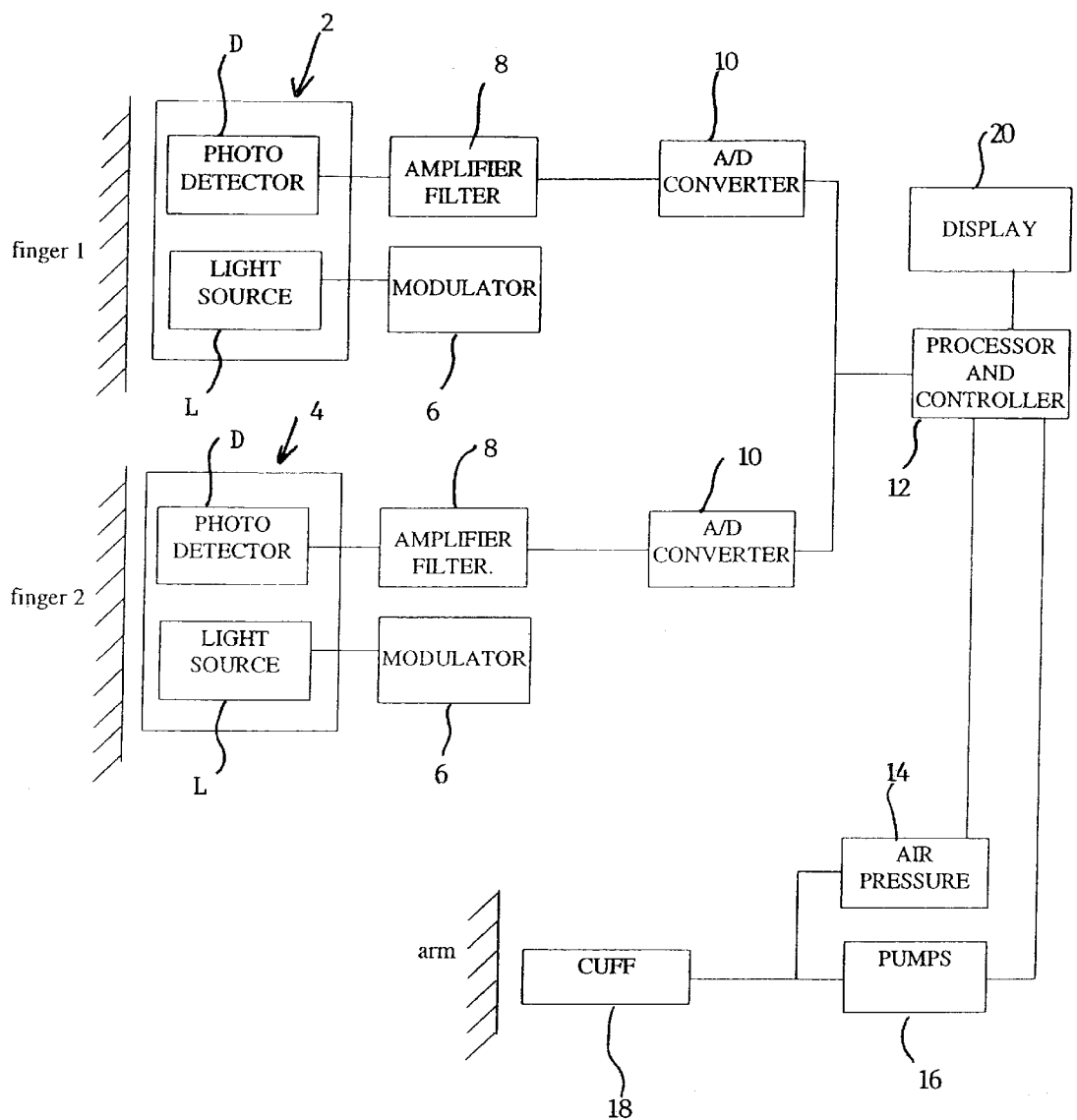

Turning now to the embodiment of FIGS. 4 and 5 in more detail, the device consists of a first PPG probe 2, fitted with per se known means for attaching the probe to a finger of one hand of a subject and similarly, a second PPG probe 4 fitted with means for attaching it to a finger of the second hand of said subject. The probes 2 and 4 each include a light source L modulated by a modulator 6 and a photodetector D, the output of which is advantageously amplified, filtered and demodulated at 8 before being digitized by an A/D converter 10. The outputs for converter 10 are applied to a processor/controller 12. The latter also governs the operation of pump 16, which affects the inflation and deflation of a pressure application means 18, e.g., a cuff, configured to be attached to the arm of one of the subject's hands and receives information from an air pressure monitor 14. While the modulator 6, amplifiers/filters 8 and A/D converters 10 are shown for the sake of clarity as being a separate assembly, it should be understood that in practice, these functions are performed by circuits physically constituting parts of the processor/controller 12. The device also includes a display 20 for displaying the arterial blood pressure and other selectable, useful information.

Figure 6:
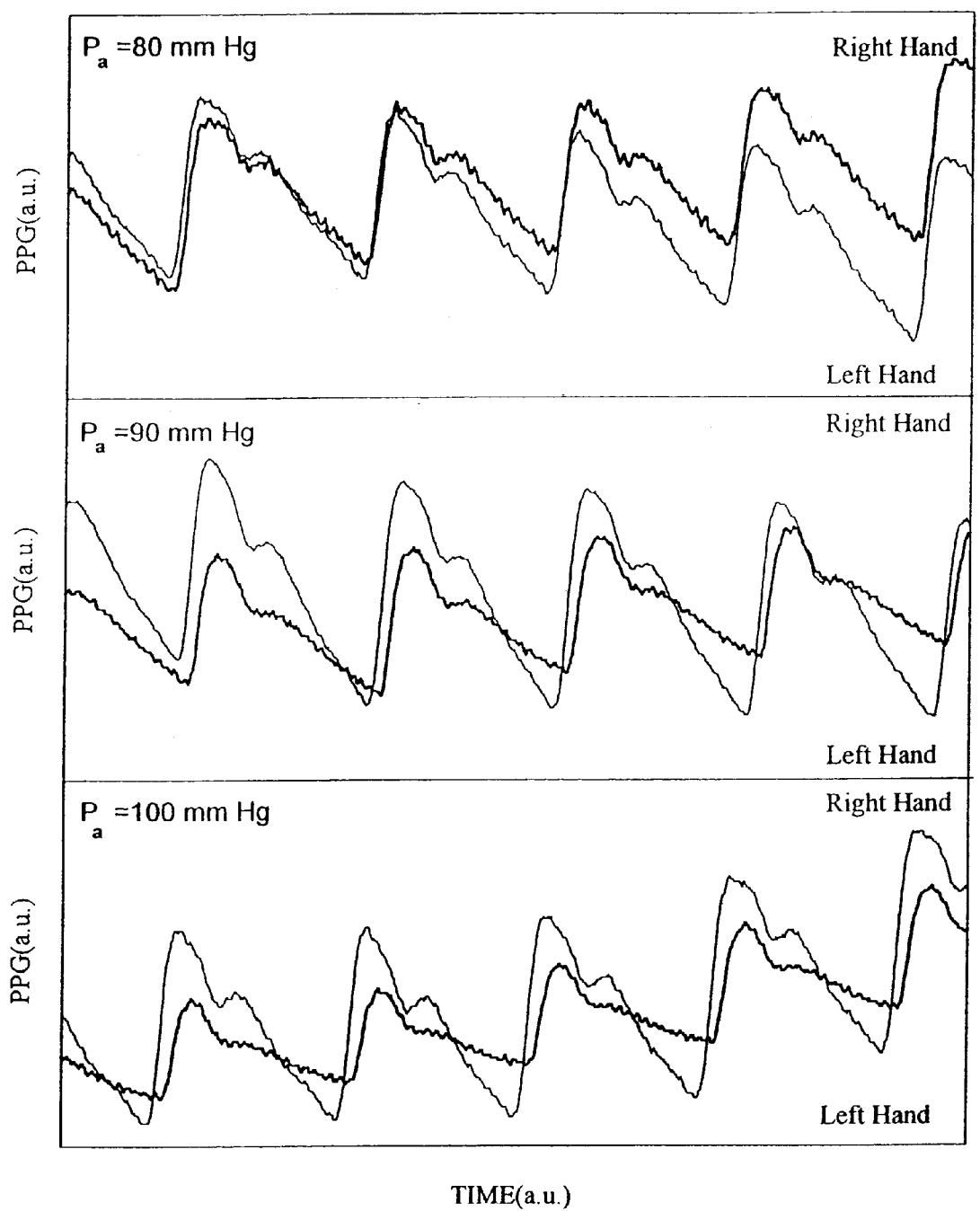

FIG. 6 shows the PPG signals in the fingers of both the right and left hands simultaneously measured when a pressure application means 18 is attached to the right arm and the air pressure in it is between the systolic and diastolic blood pressures. In the right hand curve a delayed onset of pulses as well as a reduced amplitude and area of pulses of the PPG signal when the external air pressure exceeds the diastolic ABP can be clearly seen.

As explained above, the basis for the invention is to compare the onset time of the first PPG signal in the first site which is distal to the pressure application means with that of another reference signal in the second site which is not affected by the pressure of means 18, or which is affected in a different manner from the signal of the first site. Hence, the measurement of the diastolic blood pressure can also be obtained by changing the pressure in the pressure application means and measuring the resultant delay between the first and the second PPG signals by using two PPG probes on the same limb, one distal to means 18 and the other proximal to it.

Figure 7:
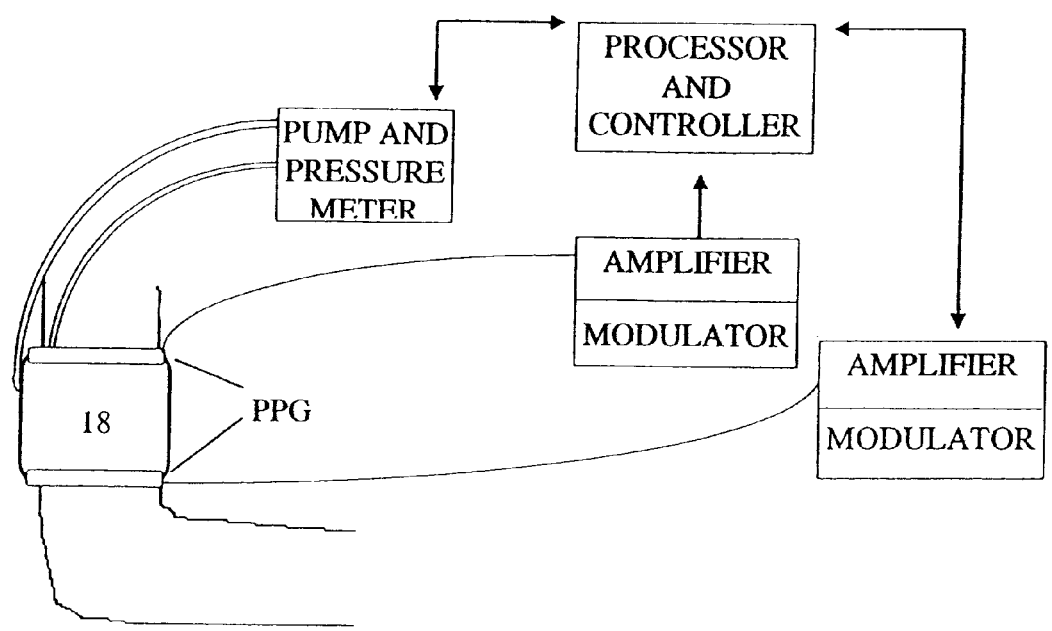

Accordingly, and with reference to FIG. 7, there is shown an embodiment similar to the embodiment of FIG. 4, however, in which the PPG probes 2 and 4 are attached to the subject's arm on both edges of the pressure application means 18, instead of on the fingers of both hands, as seen in FIG. 3. Thus, a combined pressure application means 18 and PPG probes may be formed, which can be affixed at any suitable location on a subject's body in such a way that one of the PPG probes, e.g., probe 2, will be located to provide measurements of light absorption in tissue distal to the pressure application means 18 relative to the heart, while the other PPG probe 4 will be located to provide measurements of light absorption in tissue proximal thereof.

FIGS. 8 and 9 illustrate another embodiment of the device in accordance with the present invention, in which the PPG probe 2, which measures the blood volume changes which are affected by the pressure application means 18, is attached to the skin of the forearm under the pressure application means. The second probe 4, which measures the blood volume changes which are not affected by the pressure application means 18, is attached to the skin of the contralateral forearm. The signals of the two probes are compared, and the time delay is analyzed as described herein.

While the above preferred embodiments specifically utilize the measurement of the systolic increase of tissue blood volume by the PPG probes, it should be noted that other plethysmography sensors such as electrical impedance plethysmography sensors may equally be used. Furthermore, it should be understood that non-invasive detectors of another cardiovascular parameter, such as blood flow, blood velocity or tissue blood pressure, could be utilized.

Parenthetically, it should also be noted that, while reference is made herein to preferred examples in which measurements are made while decreasing the applied air pressure, alternative embodiments may be implemented in which measurements are taken while increasing the pressure.

As mentioned above, evaluation of the time-delay between corresponding pulses of the two signals is non-trivial and, particularly in the case of noisy outputs from non-invasive sensors, cannot be performed by the simplistic approach presented by the Geddes et al. reference mentioned above. In order to provide a practical and accurate device and method, the present invention preferably performs preprocessing in the form of various smoothing functions followed by one or more of a number of techniques for measuring the time delay, examples of which will now be described.

For conciseness of presentation, each technique will be described here in algorithmic terms only. The practical details of an implementation, as well as the hardware required for implementing processor 12b, will be clear to one ordinarily skilled in the art from the algorithms described. Typically, a microprocessor unit is employed operating conventional computational software under a suitable operating system. Alternatively, a custom hardware implementation, or a combination of hardware and software (referred to as "firmware") may be used.

Turning first to the preprocessing, problems of noise common in PPG signals are preferably minimized by one or more smoothing function. In a first preferred embodiment, initial smoothing is achieved by employing a high initial sampling rate followed by averaging of groups of readings to obtain a lower effective sampling rate. In a typical example, readings may be taken at a rate of 5 kHz followed by averaging of groups of 5 readings, giving an effective sampling rate of 1 kHz. Additionally, or alternatively, smoothing algorithms are applied which do not alter the effective sampling rate. A simple example of such an algorithm is averaging over a sliding window. Thus in the typical example mentioned above, each of the 1000 readings per second may be set to a value corresponding to an average of itself together with about 20 preceding values and about 20 subsequent values.

The overall effect of such preprocessing is preferably to remove, or minimize the effect of, any noise or other transient features which have frequencies one or more orders of magnitude higher than those of the pulse rate. Thus, in preferred implementations, the preprocessing removes or attenuates at least those components of the signals with frequencies in excess of about 100 Hz, and preferably those with frequencies in excess of about 25 Hz.

Turning now to specific examples of techniques for evaluating the delay, it is a preferred feature of the present invention that the local minimum is not relied upon as a reference point to evaluate the time delay, thereby avoiding a substantial cause of inaccuracy in the approach presented by Geddes et al. Instead, the present invention either employs an alternative reference point such as will be described with reference to FIGS. 10–12, or an alternative technique such as will be described thereafter.

A first preferred approach, illustrated in FIG. 10, entails measuring the amplitude $A_1$ of a pulse of the first signal and identifying a first point in the systolic increase portion of the pulse at which the first signal reaches a predefined proportion, in this case 0.1, of the amplitude $A_1$. The same is done for the corresponding pulse of the second signal, thereby identifying a point in the systolic increase portion of the corresponding pulse at which the second signal reaches the same predefined proportion of an amplitude $A_2$, where $A_2$ is the amplitude of the corresponding pulse of the second signal. The time delay $\Delta t$ is then identified as the time between these two points.

A second preferred approach, illustrated in FIG. 11, employs taking the derivative of the systolic increase portion of each PPG curve and finding the maximum values $d1_{max}$ and $d2_{max}$ of the derivative for each. The point on each derivative curve at which the derivative reaches a predetermined proportion, in this case 50%, of its maximum value is then taken as a reference point for determining the delay. In the example shown here, these reference points are identified as $d1_{max/2}$ and $d2_{max/2}$.

A third preferred approach, illustrated in FIG. 12, employs a geometrical construct to generate a well-defined reference point in the region of the local minimum of the signals. This approach may be regarded as sharpening the minimum to a point to obtain a well defined adjusted minimum point. One particularly straightforward and advantageous implementation of this approach is to fit a straight line, by least squares approximations or other techniques, to portions of the signal slightly before and after the minimum. In one preferred implementation which has been found to give good results, straight lines were fitted to portions of the signals between about 20–50 ms before and after the minimum.

As mentioned above, the present invention also provides alternative techniques which avoid the need to define a specific reference point in the signals. In a primary example, this is done by evaluating a correlation coefficient employing the entirety of the pulse signals. Specifically, a measure of correlation between corresponding pulses of the first and second signals is evaluated as a function of a time shift of the second signal relative to the first signal. The time shift which generates a maximum value of the measure of correlation, is then defined as the delay between the pulses.

By way of example, the correlation coefficient for two sampled functions X and Y with lag $\tau$ between them may be calculated by comparing the two series $x(n)$ and $y(n)$, ($n=1, 2, 3, \ldots N$, where N is the number of the PPG pulses) after removing the last $\tau$ terms of the $x(n)$ series and the first $\tau$ terms of the $y(n)$ series. Hence the two series to be compared are:

$$x(1), x(2), \ldots x(N-\tau) \text{ and } y(\tau+1), y(\tau+2), \ldots y(N).$$

Then, a correlation coefficient (CC) may be expressed as a function of $\tau$ by:

$$CC(\tau) = \sum_{n=\tau+1}^{N} [x(n-\tau) - x_m][y(n) - y_m] / A^{\frac{1}{2}} \quad 0 \leq \tau$$

where $x_m$, $y_m$ are the mean value of $x(n)$ and $y(n)$ and $$A = \sum_{n=\tau+1}^{N} [x(n-\tau) - x_m]^2 \sum_{n=\tau+1}^{N} [y(n) - y_m]^2.$$

For negative values of $\tau$, a similar formula may be used. The lag of maximal correlation coefficient is taken as the lag between the two parameters.

By one or more of the above techniques and/or other techniques, values of the delay between the PPG signals are calculated for a range of applied cuff pressures from above the expected systolic blood pressure to below the expected diastolic blood pressure values. Optionally, one or more additional stage of smoothing may be applied, firstly to the cuff pressure as a function of time so as to remove peaks due to the pulse, and secondly to the time delay itself as a function of pressure. The time delay values are also normalized by subtracting a baseline delay value corresponding to the delay measured when substantially no pressure is applied to the cuff.

The techniques described above have been found experimentally to give very similar results. By way of example, FIGS. 13 and 14 show the variation of $\Delta t$ with applied cuff pressure as determined by the techniques of FIGS. 10 and 11, respectively.

Once this information is determined, the diastolic blood pressure is identified according to the predefined non-zero value of delay measured relative to said baseline value. Through extensive research with many subjects, it has been found that the first diastolic blood pressure, equivalent to that identified by the conventional auscultatory method, consistently corresponds to a delay of between about 30 and about 40 ms, and most preferably about 35 ms, above the baseline delay. Similarly, the second diastolic blood pressure, equivalent to that identified by the conventional auscultatory method, consistently corresponds to a delay of between about 15 and about 25 ms, and most preferably about 20 ms, above the baseline delay.

While the aforementioned values of the time delay are believed to be optimal for derivation of the conventionally used diastolic blood pressure values, it should be noted that other values may alternatively be used to provide other meaningful indicators of diastolic blood pressure. Additionally, measurement at a higher value of the delay may be used together with a predetermined subtraction or addition of a pressure value to obtain estimated blood pressure values corresponding to the conventionally used values. In this context, it is noted that measurements taken in the range between about 40 and about 60 ms, and in particular at a value chosen at or near 50 ms, are advantageous due to the smoother form of the results generally obtained in those ranges.

Turning now to FIG. 15, this illustrates the principle of a variant method according to the present invention. In this case, instead of determining a value of the time delay between the two pulses, a correlation function applied directly to the two signals is used as an indication of the degree of lag between them. The function may be as defined above with a constant $\tau=0$.

More specifically, as before, the method includes generating first and second signals indicative, respectively, of cardiac induced pulsatile variations in tissue blood volume in a first region and a second region of the subject's body according to any of the devices described above. The first and second signals are then processed to derive values of a measure of correlation between pulses in the first signal and corresponding pulses in second signal. These values are adjusted by addition or subtraction of the difference between 1 and a baseline value corresponding to the correlation coefficient when no pressure is applied to the cuff such that the correlation coefficient takes a maximum value of 1. An example of the resulting values as a function of time is shown in FIG. 15.

The diastolic blood pressure is then identified as the value of the variable pressure corresponding to a value of the measure of correlation substantially equal to a predefined proportion of the baseline value. This predefined proportion is at least about 90%, i.e., 0.9 on the adjusted plot. The actual values of the correlation coefficient determined experimentally which are believed to provide accurate values corresponding to conventional diastolic blood pressure values are about 0.915 for the first diastolic pressure and about 0.955 for the second.

In an alternative implementation, the measured values may be scaled by the base-line value rather than adjusted by addition or subtraction.

Turning now to FIG. 16, it will be noted that preferred implementations of the device and method of the present invention also provide indications of the systolic blood pressure. In principle, this can be achieved trivially by sensing the cessation and recommencing of PPG pulses as the applied cuff pressure goes above and returns below the systolic pressure. In practice, however, the pulses emerge gradually from the background signal noise in a manner which renders it difficult to identify a clear cut-off for the systolic pressure.

To address this problem, the present invention preferably provides a method to quantify the reappearance of the PPG signal. To this end, the PPG pulses occurring before the cuff pressure increase are used as a reference. A number of pulses, typically between about 4 and about 10 pulses, are recorded and their mean amplitude (or area) is stored. The systolic blood pressure is then taken as the cuff pressure for which the amplitude of PPG signals (or their area) is a predefined proportion of the stored mean amplitude (or area). A proportion of about 8–10% has been found sufficient to distinguish the signal from background noise while providing sufficiently accurate results.

FIGS. 17A–17C illustrate the comparison between the present method (by use of 0.1 of the amplitude) and sphygmomanometry which is the "gold standard". The average and standard deviation of the difference between the two methods are as follows:

|  | mean difference (mmHg) | standard deviation (mmHg) |
| --- | --- | --- |
| Systolic | −1.9 | 3.4 |
| Diastolic | −1.5 | 4.9 |

These compare favorably with the standards set by AAMI (US) and BSH (UK). By way of example, the standards required by AAMI are a maximum mean difference of ±5 mmHg and a maximum standard deviation of 8 mmHg. A good accuracy has been achieved in reproducing the systolic and diastolic arterial blood pressure values using the device and methods of the present invention in a reasonable range of pressures.

While in the above embodiments the pressure application means has been shown and described to be attached to a subject's arm, it should be understood that it can just as well be attached to a subject's hand, leg, ankle or foot, arms and legs being referred to collectively as limbs. Similarly, it should be understood that the measurement probes of the present invention may be attached to a subject's legs, feet or toes. Fingers and toes are referred to collectively as digits.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Finally, turning to FIGS. 18 and 19, it should be noted that the devices of the present invention facilitate implementation as a compact, non-intrusive device which can be worn by a patient for continuous or intermittent monitoring of blood pressure for extended periods without interfering with other activities. To this end, the implementations of FIGS. 18 and 19 preferably employ PPG sensors formed as rings which can be worn non-intrusively on a finger of each hand. The main electronic control and processing elements are preferably implemented as a separate box which can conveniently be worn on a belt or the like.

In the implementation of FIG. 18, connections between the PPG sensors, the cuff and the control box are made via wires passing up the arms. These may be taped or otherwise attached to the skin beneath clothing in a manner generally non-disruptive to a wide range of activities.

FIG. 19 shows a further option in which some, or preferably all, of the components are associated via wireless connections, typically at radio frequencies. The miniature transmitter and receiver components required for such implementations are widely available, as will be clear to one ordinarily skilled in the art.

It will be appreciated that the above descriptions are intended only to serve as examples, and that other embodiments are possible within the spirit and the scope of the present invention.

What is claimed is:

1. A method for measuring arterial diastolic blood pressure in a subject, the method comprising:
    (a) generating first and second signals indicative, respectively, of cardiac induced pulsatile variations in tissue blood volume in a first region and a second region of the subject's body;
    (b) processing said first and second signals to derive values of a delay between pulses in said first signal and corresponding pulses in second signal;
    (c) evaluating a baseline value of said delay;
    (d) applying a variable pressure to a third region of the subject's body so as to affect blood flow through at least one artery in said third region, said variable pressure being varied as a function of time, said first, said second and said third regions being chosen such that said delay varies as a function of said variable pressure; and
    (e) identifying a value of said variable pressure corresponding substantially to a predefined non-zero value of said delay measured relative to said baseline value.

2. The method of claim 1, wherein said predefined non-zero value of said delay is between about 30 and about 40 ms.

3. The method of claim 1, wherein said predefined non-zero value of said delay is between about 15 and about 25 ms.

4. The method of claim 1, wherein said processing includes:

(a) measuring a first amplitude of a first pulse of said first signal;

(b) identifying a first point in the systolic increase portion of said first pulse at which said first signal reaches a predefined proportion of said first amplitude;

(c) measuring a second amplitude of a corresponding pulse of said second signal;

(d) identifying a second point in the systolic increase portion of said corresponding pulse at which said second signal reaches said predefined proportion of said second amplitude; and (e) defining a value of said delay as the time between said first and said second points.

5. The method of claim 4, wherein said predefined proportion is between about 0.1 and about 0.5.

6. The method of claim 1, wherein said processing includes:

(a) calculating a time derivative of a first pulse of said first signal;

(b) identifying a first maximum value of said time derivative in the systolic increase portion of said first pulse;

(c) identifying a first point at which said time derivative reaches a predefined proportion of said first maximum value;

(d) calculating a time derivative of a second pulse of said second signal;

(e) identifying a second maximum value of said time derivative in the systolic increase portion of said second pulse;

(f) identifying a second point at which said time derivative reaches a predefined proportion of said second maximum value; and (g) defining a value of said delay as the time between said first and said second points.

7. The method of claim 1, wherein said processing includes:

(a) for corresponding pulses of each of said first and second signals,
  (i) identifying a local minimum of said signal,
  (ii) fitting a negative gradient line to a predefined portion of said signal prior to said local minimum,
  (iii) fitting a positive gradient line to a predefined portion of said signal subsequent to said local minimum, and
  (iv) extrapolating said negative gradient line and said positive gradient line to determine an intersection, referred to as an adjusted minimum point of said signal; and (b) defining a value of said delay as the time between said adjusted minimum point of said first signal and said adjusted minimum point of said second signal.

8. The method of claim 1, wherein said processing includes:

(a) evaluating a measure of correlation between corresponding pulses of said first and second signals, said measure of correlation being evaluated as a function of a time shift of said second signal relative to said first signal; and (b) defining a value of said delay as the time shift which generates a maximum value of said measure of correlation.

9. The method of claim 1, wherein said second region is chosen such that variations in said subcutaneous blood volume in said second region are substantially unaffected by variations in said variable pressure.

10. The method of claim 1, wherein said first and second signals are generated by use of non-invasive sensors.

11. The method of claim 1, wherein said first and second signals are generated by use of photoplethysmography sensors.

12. The method of claim 8, wherein said variable pressure is applied using an inflatable cuff, and wherein at least one of said photoplethysmography sensors is attached to said cuff.

13. The method of claim 1, wherein said first and second signals are generated by use of impedance plethysmography sensors.

14. A device for measuring arterial diastolic blood pressure in a subject, the device comprising:

(a) a pressure cuff applicable to a first region of the subject's body so as to affect blood flow through at least one artery in said first region;

(b) a pressure controller operatively connected to said pressure cuff so as to vary a current pressure of said pressure cuff;

(c) first and second plethysmography sensors for application to a second region and a third region of the subject's body, said first and second plethysmography sensors being configured to produce first and second signals, respectively, indicative of pulsatile variations in tissue blood volume in said second and third regions, respectively; and (d) a processor associated with said pressure controller and with said first and second plethysmography sensors, said processor being configured to:
  (i) process said first and second signals to derive values of a delay between pulses in said first signal and corresponding pulses in second signal,
  (ii) evaluate a baseline value of said delay corresponding to a current pressure substantially equal to ambient pressure, and
  (iii) identify as the diastolic pressure a value of said variable pressure corresponding substantially to a predefined non-zero value of said delay measured relative to said baseline value.

15. A method for measuring arterial diastolic blood pressure in a subject, the method comprising:

(a) generating first and second signals indicative, respectively, of cardiac induced pulsatile variations in tissue blood volume in a first region and a second region of the subject's body;

(b) processing said first and second signals to derive values of a measure of correlation between pulses in said first signal and corresponding pulses in second signal;

(c) applying a variable pressure to a third region of the subject's body so as to affect blood flow through at least one artery in said third region, said variable pressure being varied as a function of time, said first, said second and said third regions being chosen such that said measure of correlation varies as a function of said variable pressure; and (d) identifying a value of said variable pressure corresponding to a value of said measure of correlation substantially equal to a predefined value.

16. The method of claim 15, further comprising evaluating a baseline value of said measure of correlation, said measure of correlation being adjusted on the basis of said baseline value such that said measure of correlation approaches 1 at low values of said variable pressure.

17. The method of claim 15, wherein said predefined value is at least about 0.9.

* * * * *